US012310305B2

(12) United States Patent
Ganci, Jr. et al.

(10) Patent No.: US 12,310,305 B2
(45) Date of Patent: May 27, 2025

(54) AIRFLOW CONTROL FOR AGRICULTURAL POLLINATION

(71) Applicant: International Business Machines Corporation, Armonk, NY (US)

(72) Inventors: John M. Ganci, Jr., Raleigh, NC (US); Sarbajit K. Rakshit, Kolkata (IN); Martin G. Keen, Cary, NC (US); Jeremy R. Fox, Georgetown, TX (US)

(73) Assignee: International Business Machines Corporation, Armonk, NY (US)

( * ) Notice: Subject to any disclaimer, the term of this patent is extended or adjusted under 35 U.S.C. 154(b) by 317 days.

(21) Appl. No.: 17/939,220

(22) Filed: Sep. 7, 2022

(65) Prior Publication Data

US 2024/0074370 A1 Mar. 7, 2024

(51) Int. Cl.
*G06K 9/00* (2022.01)
*A01H 1/02* (2006.01)

(52) U.S. Cl.
CPC .................................. *A01H 1/027* (2021.01)

(58) Field of Classification Search
CPC ......... G01N 33/0098; G01N 2223/618; G01N 2021/8466; G01N 2223/619; G01N 2223/621; G06T 2207/30128; G06T 7/00; G06V 20/68; G06V 10/10; G06V 10/20; G06V 10/22; G06V 10/225; G06V 10/23;
(Continued)

(56) References Cited

U.S. PATENT DOCUMENTS 8,602,837 B1 12/2013 Allan
11,270,189 B2 3/2022 Wachira
(Continued)

FOREIGN PATENT DOCUMENTS

JP 2021153402 A 10/2021
WO 2022049580 A1 3/2022

OTHER PUBLICATIONS

Nguyen, Hai Cong, et al. "A method for automatic honey bees detection and counting from images with high density of bees." 2022 IEEE Ninth International Conference on Communications and Electronics (ICCE). IEEE, 2022. (Year: 2022).*
(Continued)

*Primary Examiner* — Avinash Yentrapati
(74) *Attorney, Agent, or Firm* — Matthew Zehrer

(57) ABSTRACT

A computer-implemented method for airflow control for agricultural pollination is disclosed. The computer-implemented method includes performing image analysis on an agricultural image to determine a type and classification of one or more plants in the agricultural image, determining one or more pollination requirements for the one or more determined plants, determining one or more current airflow parameters within a predetermined area of the one or more plants in the agricultural image, determining one or more optimal airflow parameters based on the type of plants in the agricultural image, the classification of plants in the agricultural image, the one or more pollination requirements for the plants in the agricultural image, and the one or more current airflow parameters, and generating an automatic airflow adjustment model for optimizing the airflow parameters for the plants based, at least in part, on the one or more determined optimal airflow parameters.

20 Claims, 6 Drawing Sheets

(58) Field of Classification Search
CPC ...... G06V 10/255; G06V 10/54; G06V 10/56; G06V 10/60; G06V 10/70; G06V 10/765; G06V 10/764; G06V 20/60; G06V 20/69; G06F 18/00
See application file for complete search history.

(56) References Cited

U.S. PATENT DOCUMENTS

| | | | |
|---|---|---|---|
| 2020/0045895 A1 | 2/2020 | Shahak Ravid | |
| 2020/0134741 A1 | 4/2020 | Bongartz et al. | |
| 2020/0184153 A1* | 6/2020 | Bongartz | A01G 9/249 |
| 2021/0185942 A1* | 6/2021 | Sibley | G06T 7/0012 |
| 2021/0187532 A1* | 6/2021 | Sibley | B05B 13/005 |
| 2021/0192754 A1* | 6/2021 | Sibley | A01B 79/005 |
| 2022/0000051 A1* | 1/2022 | Geltner | A01G 7/06 |
| 2022/0183208 A1* | 6/2022 | Sibley | G05D 1/0246 |
| 2022/0237481 A1* | 7/2022 | Jones | G06V 10/7788 |

OTHER PUBLICATIONS

"Air Pressure and Wind", link provided by NOAA: The National Oceanic and Atmospheric Administration, downloaded from the Internet May 17, 2022, 11 pages, <https://www.weather.gov/media/zhu/ZHU_Training_Page/winds/pressure_winds/pressure_winds.pdf>.
"Can Artificial Intelligence promote and automate pollination?", Mindsync, Apr. 23, 2021, 5 pages, <https://medium.com/mindsync-ai/can-artificial-intelligence-promote-and-automate-pollination-a8405f5025d0>.
"Environmental factors affecting plant growth", OSU Extension Service, downloaded from the Internet May 17, 2022, 10 pages, <https://extension.oregonstate.edu/gardening/techniques/environmental-factors-affecting-plant-growth>.
"Honey Bees & Pollination", National Honey Board, downloaded from the Internet May 17, 2022, 2 pages, <https://honey.com/bees-sustainability/honey-bees-pollination>.
"Plant-pollinator interactions database for construction of potential networks", Environmental Information Data Centre, Last updated Jun. 30, 2021, 3 pages, <https://data.gov.uk/dataset/11cff012-72f2-4d47-b323-1121e5f35ebb/plant-pollinator-interactions-database-for-construction-of-potential-networks>.
"Pollination", USGS Science Data Catalog, downloaded from the Internet May 17, 2022, 3 pages, <https://data.usgs.gov/datacatalog/browse/topics/pollination>.
"Search for Pollinators", Center for Plant Conservation, downloaded from the Internet May 17, 2022, 4 pages, < https://saveplants.org/pollinator-search/>.
"The Why, What, When, Where, Who, How of Pollination", Smithsonian Gardens, downloaded from the Internet May 17, 2022, 4 pages, <https://gardens.si.edu/gardens/pollinator-garden/why-what-when-where-who-how-pollination/>.
Why Are Honeybees Disappearing?, Earth Talk, Updated on Mar. 31, 2018, 2 pages, <https://www.thoughtco.com/why-honeybees-are-disappearing-1203584>.
Cooper, Rachel, "10 Innovations in Agriculture", Oct. 19, 2021, 8 pages, <https://www.climateaction.org/news/10-innovations-in-agriculture1>.
Cresswell et al., "The aerodynamics and efficiency of wind pollination in grasses", Functional Ecology, vol. 24, Issue 4, 19 pages, First published: Jul. 13, 2010, <https://besjournals.onlinelibrary.wiley.com/doi/full/10.1111/j.1365-2435.2010.01704.x>.
Dol, Godfrey, "Without proper pollination, all greenhouse techniques are reduced to nothing", horti daily, Publication date: Wed Jan. 15, 2020, 6 pages, <https://www.hortidaily.com/article/9179681/without-proper-pollination-all-greenhouse-techniques-are-reduced-to-nothing/>.
Ellis, Jack, "Better than bees? Arugga nets $4m for its indoor farm pollination robots", Jun. 2, 2021, 9 pages, <https://agfundernews.com/arugga-nets-4-million-for-its-indoor-pollinating-robots>.
Goldammer, Ted, "Greenhouse Management, A Guide to Operations and Technology", Chapter 5, "Green house Ventilation and Cooling" 3 pages, Apex Publishers, downloaded from the Internet May 17, 2022, <http://www.greenhouse-management.com/greenhouse_management/greenhouse_ventilation_cooling/forced_air_ventilation.htm>.
Grossman, Elizabeth, "Declining Bee Populations Pose a Threat to Global Agriculture", Yale Environment 360, Apr. 30, 2013, 6 pages, < https://e360.yale.edu/features/declining_bee_populations_pose_a_threat_to_global_agriculture>.
IBM, "IBM Environmental Intelligence Suite—Regenerative Agriculture" downloaded from the Internet May 17, 2022, 7 pages, <https://www.ibm.com/products/environmental-intelligence-suite/agriculture>.
IBM, "IoT Solutions", downloaded from the Internet May 17, 2022, 8 pages, <https://www.ibm.com/cloud/internet-of-things>.
IBM, "Maximo Application Suite—Remote Asset Monitoring", downloaded from the Internet May 17, 2022, 8 pages, <https://www.ibm.com/products/maximo/remote-monitoring>.
Jacobo, Julia, "Nearly 40% decline in honey bee population last winter 'unsustainable', experts say", Jul. 9, 2019, 9 pages, <https://abcnews.go.com/US/40-decline-honey-bee-population-winter-unsustainable-experts/story?id=64191609>.
Klein, Alice, "Robotic bee could help pollinate crops as real bees decline", downloaded from the Internet May 17, 2022, 1 page, <https://www.newscientist.com/article/2120832-robotic-bee-could-help-pollinate-crops-as-real-bees-decline/>.
Lu et al., "TasselNetV2+: A Fast Implementation for High-Throughput Plant Counting From High-Resolution RGB Imagery", Frontiers in Plant Science, published: Dec. 7, 2020, doi: 10.3389/fpls.2020.541960, vol. 11, Article 541960, 15 pages, <https://www.frontiersin.org/articles/10.3389/fpls.2020.541960/full>.
Megan, "How to Tell if a Plant is Pollinated", Updated Oct. 30, 2019, SFGATE, 10 pages, <https://homeguides.sfgate.com/tell-plant-pollinated-34828.html>.
Mell et al., "The NIST Definition of Cloud Computing", Recommendations of the National Institute of Standards and Technology, NIST Special Publication 800-145, Sep. 2011, 7 pages.
Phillips, Benjamin, "Bumble bees in greenhouse vegetable production", Apr. 12, 2019, 9 pages, MSU Extension, <https://www.canr.msu.edu/news/bumble-bees-in-greenhouse-vegetable-production>.
Pond Mentzer, Alissa, "What is the Range of Barometric Pressure?", Updated Apr. 24, 2017, 8 pages, <https://sciencing.com/range-barometric-pressure-5505227.html>.
Shahbandeh, M., "Indoor farming-statistics & facts", Mar. 10, 2022, 4 pages, <https://www.statista.com/topics/4467/indoor-farming/#dossierKeyfigures>.
Vinjie, E., "High Altitude Gardening", Planet Natural Research Center, downloaded from the Internet on May 17, 2022, 11 pages, <https://www.planetnatural.com/high-altitude-gardening/>.
Volente, Greg, "How to Pollinate Indoor Plants", Greenhouse Today, downloaded from the Internet on May 17, 2022, 13 pages, <https://www.greenhousetoday.com/how-to-pollinate-indoor-plants/>.
Soffar, H., Types of pollination in the plants, What is self and cross pollination?, Retrieved from: https://www.online-sciences.com/the-living-organisms/the-types-and-methods-of-pollination-in-the-plants/, Apr. 20, 2015, 9 pages.

* cited by examiner

AIRFLOW CONTROL FOR AGRICULTURAL POLLINATION

BACKGROUND

The present invention relates generally to the field of plant pollination, and more particularly to, airflow control for optimized agriculture pollination.

Pollination is an essential part of plant reproduction and agriculture. Pollen from a flower's anthers, the male part of the plant, rubs or drops onto a pollinator. The pollinator then takes this pollen to another flower, where the pollen sticks to the stigma, the female part of the plant. The fertilized flower later yields fruit and seeds. Different types of plants grow at different rates and require pollination at different timelines.

There are many different means by which plants can be pollinated, such as wind pollination, animal pollination, water pollination, and robotic/manual pollination. Conifers and about 12% of flowering plants are wind pollinated. About 80% of flowering plants, including 35% of our food crops, are animal pollinated. Approximately 200,000 animal species act as pollinators, including about 3,500 species of native bees, 1,000 species of hummingbirds, as well as bats, small mammals and all manner of insects. Water pollination can take place both underwater and on the surface. In both cases, large amounts of pollen are released and depend on currents or breezes to bring it in contact with a receptive stigma. Robotic or manual pollination devices can also mimic honeybee pollination.

Approximately one-third of the human diet is derived from insect-pollinated plants, and honeybees are responsible for about 80 percent of this type of pollination. Within the USA alone, honeybees are responsible for the pollination of nearly 20 billion USD worth of crop production (flowering plants, fruits and vegetables).

Declining honeybee populations have led scientists to research the consequences of the rapid decline, while also researching ways to mitigate the negative effects that this decline has on farming management and production. Indoor farming that uses an enclosed environment such as a greenhouse or indoor agriculture facility is one method that can be used to mitigate declining honeybee populations.

In addition to the noted honeybee decline, there are other reasons that agriculture farming is being adapted to use indoor environments where growing conditions can be managed, including: using less water and chemicals, making crops less vulnerable to changes in the climate, and producing more reliable yields.

WO2022049580A1 describes "artificial pollination of a flowering plant in need of pollination." This references discusses "generating vibration at the flowering plant by the vibration element, activating the airflow-generating element to create a cloud of pollen grains in the vicinity of the flowering plant; and applying an electrostatic force to the pollen grains of the flowering plants by the electrostatic force generating element." Embodiments of the present invention are advantageous and recognize the need and importance of determining if there is a presence of bees in the pollination area to assist with pollination.

SUMMARY

According to one embodiment of the present invention, a computer-implemented method for airflow control for agricultural pollination is disclosed. The computer-implemented method includes performing image analysis on an agricultural image to determine a type of one or more plants in the agricultural image and a classification of one or more plants in the agricultural image. The computer-implemented method further includes determining one or more pollination requirements for the one or more determined plants in the agricultural image. The computer-implemented method further includes determining one or more current airflow parameters within a predetermined area of the one or more plants in the agricultural image. The computer-implemented method further includes determining one or more optimal airflow parameters based, at least in part, on the type of one or more plants in the agricultural image, the classification of one or more determined plants in the agricultural image, the one or more pollination requirements for the one or more determined plants in the agricultural image, and the one or more current airflow parameters. The computer-implemented method further includes generating an automatic airflow adjustment model for optimizing the airflow parameters for the one or more determined plants based, at least in part, on the one or more determined optimal airflow parameters.

According to another embodiment of the present invention, a computer program product for airflow control for agricultural pollination is disclosed. The computer program product includes one or more computer readable storage media and program instructions stored on the one or more computer readable storage media. The program instructions include instructions to perform image analysis on an agricultural image to determine a type of one or more plants in the agricultural image and a classification of one or more plants in the agricultural image. The program instructions further include instructions to determine one or more pollination requirements for the one or more determined plants in the agricultural image. The program instructions further include instructions to determine one or more current airflow parameters within a predetermined area of the one or more plants in the agricultural image. The program instructions further include instructions to determine one or more optimal airflow parameters based, at least in part, on the type of one or more plants in the agricultural image, the classification of one or more determined plants in the agricultural image, the one or more pollination requirements for the one or more determined plants in the agricultural image, and the one or more current airflow parameters. The program instructions further include instructions to generate an automatic airflow adjustment model for optimizing the airflow parameters for the one or more determined plants based, at least in part, on the one or more determined optimal airflow parameters.

According to another embodiment of the present invention, a computer system for airflow control for agricultural pollination is disclosed. The computer system includes one or more computer processors, one or more computer readable storage media, and computer program instructions, the computer program instructions being stored on the one or more computer readable storage media for execution by the one or more computer processors. The program instructions include instructions to perform image analysis on an agricultural image to determine a type of one or more plants in the agricultural image and a classification of one or more plants in the agricultural image. The program instructions further include instructions to determine one or more pollination requirements for the one or more determined plants in the agricultural image. The program instructions further include instructions to determine one or more current airflow parameters within a predetermined area of the one or more plants in the agricultural image. The program instructions further include instructions to determine one or more optimal airflow parameters based, at least in part, on the type of one or more plants in the agricultural image, the classification of one or more determined plants in the agricultural image, the one or more pollination requirements for the one or more determined plants in the agricultural image, and the one or more current airflow parameters. The program instructions further include instructions to generate an automatic airflow adjustment model for optimizing the airflow parameters for the one or more determined plants based, at least in part, on the one or more determined optimal airflow parameters.

Embodiments of the present invention are advantageous by recognizing factors such as the type of one or more plants in the agricultural image, the classification of one or more determined plants in the agricultural image, the one or more pollination requirements for the one or more determined plants in the agricultural image, and the one or more current airflow parameters effect the optimum airflow parameters. In an embodiment, a previous crop yield and airflow parameters are determined from a type of plant in previous agricultural images and compared to the current plant and airflow parameters is advantageous to adjust the optimal airflow parameters to receive optimal pollination. An embodiment wherein determining an optimal airflow parameter is based on performing image analysis on the agricultural image to determine a density of bees in the agricultural image and adjusting the optimal airflow parameters based on the density of bees in the agricultural image is advantageous to utilize the bees to aid in pollination. An embodiment wherein adjusting the optimal airflow parameters is further based on a location of the density of bees within the predetermined area of the one or more plants in the agricultural image is advantageous to move the bees to a desired area to pollinate the plants.

BRIEF DESCRIPTION OF DRAWINGS

The drawings included in the present disclosure are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
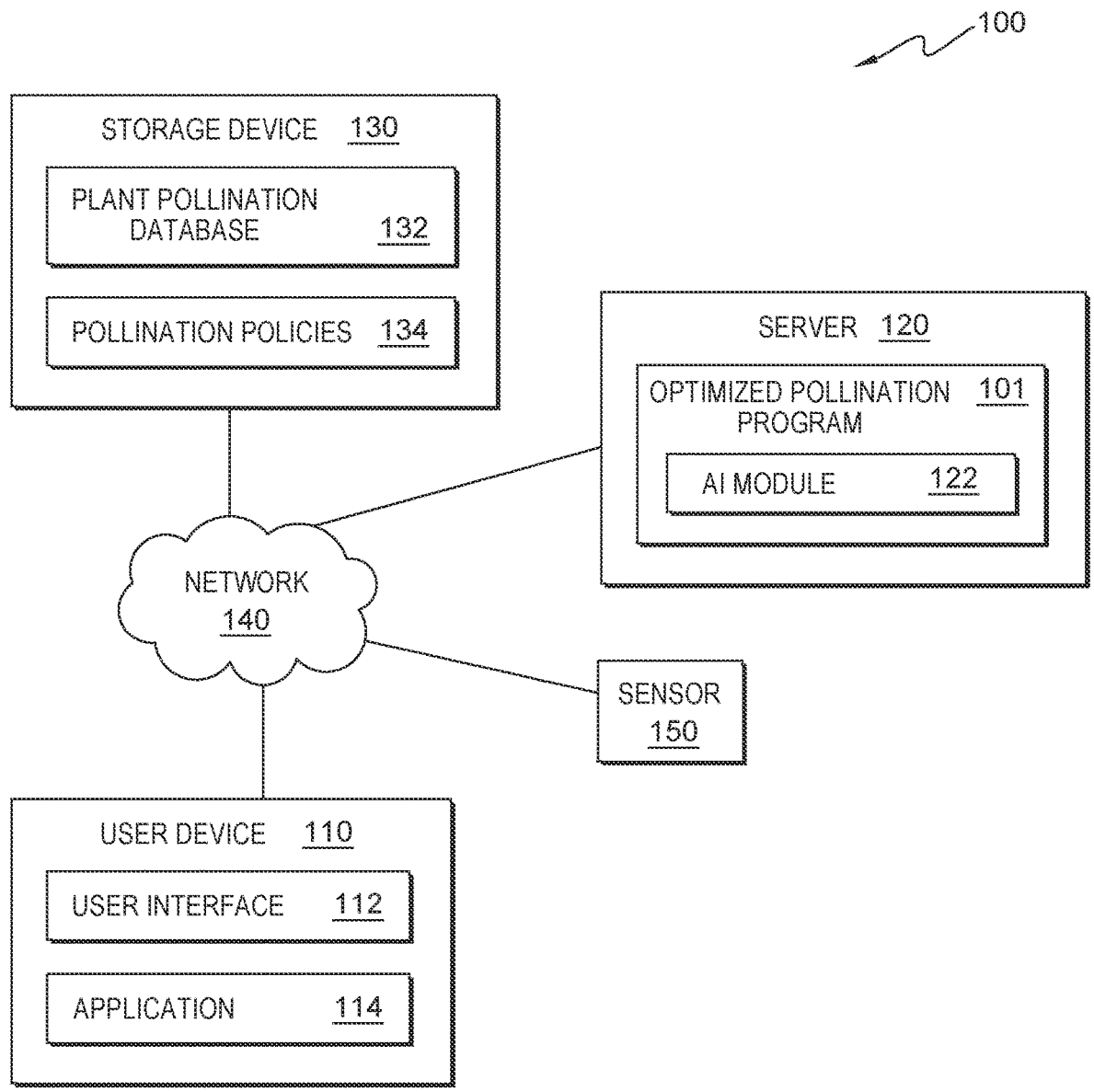
FIG. 1 is a block diagram of a network computing environment for optimized pollination program 101, generally designated 100, in accordance with at least one embodiment of the present invention.

While the embodiments described herein are amenable to various modifications and alternative forms, specifics thereof have been shown by way of example in the drawings and will be described in detail. It should be understood, however, that the particular embodiments described are not to be taken in a limiting sense. On the contrary, the intention is to cover all modifications, equivalents, and alternatives falling within the spirit and scope of the disclosure.

DETAILED DESCRIPTION

The present invention relates generally to the field of plant pollination, and more particularly to, airflow control for optimized agriculture pollination.

Declining honeybee populations have led scientists to research the consequences of the rapid decline, while also researching ways to mitigate the negative effects that this decline has on farming management and production. Indoor farming that uses an enclosed environment such as a greenhouse or indoor agriculture facility is one method that can be used to mitigate declining honeybee populations.

In addition to the noted honeybee decline, there are other reasons that agriculture farming is being adapted to use indoor environments where growing conditions can be managed, including: using less water and chemicals, making crops less vulnerable to changes in the climate, and producing more reliable yields.

Indoor farming provides an environment that the bees can be used for pollination and protected from environmental sources that have devastated bee populations by as much as 70%. Bees are widely used for indoor farming pollination for efficiency and low cost. Embodiments of the present invention recognize that there are other methods of pollination that are possible such as human or robotic based pollination. Human pollination methods are very labor intensive and not cost effective on large scale. Robotic method pollination methods require significant investment and adaption of the environment for the robots to perform the pollination. Embodiments of the present invention recognize bees are widely used and cost effective. Embodiments of the present invention should account for integration with an environment that uses bees for pollination as one of the possible methods for pollination. However, this does not exclude integration with other methods of pollination.

Embodiments of the present invention recognize a need for an AI enabled wind flow control for optimizing agriculture pollination in enclosed farming environments. Embodiments of the present invention perform image analysis of flowering plants to determine airflow control and timing of airflow control affect pollination of agricultural plants and flowers. Embodiments of the present invention determine the completeness of pollination or pollination stage of the flowering plants by image analysis and sensor data analysis. Pollination stages can include any growth stage or growth progression of a plant. Such as budding, size of a bud, flower, or leaf, and duration since planting or budding. Embodiments of the present invention identify the appropriate timing of controlled airflow by analyzing the images of the flowers. Embodiments of the present invention are advantageous by analyzing and identifying whether flowers have bloomed above a predetermined threshold and determine when pollination can be started and the duration of the controlled airflow.

Embodiments of the present invention recognize the need for an AI enabled wind flow control for optimized agriculture pollination in enclosed farming environments with or without bees. Embodiments of the present invention account for scenarios where bees are and are not present in the environment. In a controlled environment, such as a greenhouse for agricultural farming, bees may not be available for pollination and/or not distributed in areas needed for optimized pollination. Embodiments of the present invention identify whether bees are present in the enclosed farming environment, and accordingly dynamically adapt the airflow parameters within the enclosed environment to ensure that the bee pollination is not negatively impacted by the natural or artificially adapted airflow. Embodiments of the present invention are advantageous because they account for the possibility of the lack of wind flow in controlled environments. In a controlled environment such as a greenhouse, natural wind or airflow may not be available or sufficient for optimal pollination. This lack of airflow can have a negative impact on plant pollination, growth, and crop yield.

Embodiments of the present invention learn, through AI, optimal wind flow parameters for optimized pollination and crop yield. Embodiments of the present invention track and learn the effectiveness of pollination by evaluating the yield of crops, applied air flow parameters, etc, and accordingly create a knowledge corpus to identify how effective pollination can be performed.

Embodiments of the present invention capture data and stream the captured data to an AI system for analysis. Embodiments of the present invention perform AI image, audio and wind flow analysis with respect pollination of agricultural plants and flowers. Embodiments of the present invention determine programmatic control of wind flow to optimize plant pollination. Embodiments of the present invention recognize different plants require pollination at different times. For example, some plants have larger or shorter windows for pollination or require pollination sooner or farther from being planted. Embodiments of the present invention determine whether the plant is at a particular growth stage above a predetermined threshold, and thereby, whether the plant is ready for pollination. Embodiments of the present invention determine AI learned wind flow parameters stored in knowledge base.

The present invention may be a system, a method, and/or a computer program product at any possible technical detail level of integration. The computer program product may include a computer readable storage medium (or media) having computer readable program instructions thereon for causing a processor to carry out aspects of the present.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suit-able combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention will now be described in detail with reference to the Figures. FIG. 1 is a functional block diagram of a network computing environment for optimized pollination program 101, generally designated 100, in accordance with at least one embodiment of the present invention. In an embodiment, network computing environment 100 may be provided by cloud computing environment 50, as depicted and described with reference to FIG. 5, in accordance with at least one embodiment of the present invention. FIG. 1 provides an illustration of only one implementation and does not imply any limitations with regard to the environments in which different embodiments may be implemented. Many modifications to the depicted environment may be made by those skilled in the art without departing from the scope of the present invention as recited by the claims.

Network computing environment 100 includes user device 110, server 120, storage device 130, and sensor 150, interconnected over network 140. User device 110 may represent a computing device of a user, such as a laptop computer, a tablet computer, a netbook computer, a personal computer, a desktop computer, a personal digital assistant (PDA), a smart phone, a wearable device (e.g., smart glasses, smart watches, e-textiles, AR headsets, etc.), or any programmable computer systems known in the art. In general, user device 110 can represent any programmable electronic device or combination of programmable electronic devices capable of executing machine readable program instructions and communicating with server 120, storage device 130 and other devices (not depicted) via a network, such as network 140. User device 110 can include internal and external hardware components, as depicted and described in further detail with respect to FIG. 4.

User device 110 further includes user interface 112 and application 114. User interface 112 is a program that provides an interface between a user of an end user device, such as user device 110, and a plurality of applications that reside on the device (e.g., application 114). A user interface, such as user interface 112, refers to the information (such as graphic, text, and sound) that a program presents to a user, and the control sequences the user employs to control the program. A variety of types of user interfaces exist. In one embodiment, user interface 112 is a graphical user interface. A graphical user interface (GUI) is a type of user interface that allows users to interact with electronic devices, such as a computer keyboard and mouse, through graphical icons and visual indicators, such as secondary notation, as opposed to text-based interfaces, typed command labels, or text navigation. In computing, GUIs were introduced in reaction to the perceived steep learning curve of command-line interfaces which require commands to be typed on the keyboard. The actions in GUIs are often performed through direct manipulation of the graphical elements. In another embodiment, user interface 112 is a script or application programming interface (API). In an embodiment, a user utilizes user device 110 to upload or view an image, video, or information about one or more plants or the environment in which the plants are located. For example, a user uploads information on the type of plants planted in the environment and their pollination facts to user device 110 via user interface 112. Such as, average time from planting to pollination or images of what a plant ready to be pollinated looks like. In an embodiment, a user views an image or video of one or more plants captured by the one or more sensors 150 located within the plant's environment.

Application 114 can be representative of one or more applications (e.g., an application suite) that operate on user device 110. In an embodiment, application 114 is representative of one or more applications (e.g., social media applications, web conferencing applications, and email applications) located on user device 110. In various example embodiments, application 114 can be an application that a user of user device 110 utilizes to view or upload plant pollination information, data, video, images, or other media. In an embodiment, application 114 can be a client-side application associated with a server-side application running on server 120 (e.g., a client-side application associated with optimized pollination program 101). In an embodiment, application 114 can operate to perform processing steps of optimized pollination program 101 (i.e., application 114 can be representative of optimized pollination program 101 operating on user device 110).

Server 120 is configured to provide resources to various computing devices, such as user device 110. In various embodiments, server 120 is a computing device that can be a standalone device, a management server, a web server, an application server, a mobile device, or any other electronic device or computing system capable of receiving, sending, and processing data. In an embodiment, server 120 represents a server computing system utilizing multiple computers as a server system, such as in a cloud computing environment. In an embodiment, server 120 represents a computing system utilizing clustered computers and components (e.g. database server computer, application server computer, web server computer, webmail server computer, media server computer, etc.) that act as a single pool of seamless resources when accessed within network computing environment 100. In general, server 120 represents any programmable electronic device or combination of programmable electronic devices capable of executing machine readable program instructions and communicating with each other, as well as with user device 110, storage device 130, sensor 150, and other computing devices (not shown) within network computing environment 100 via a network, such as network 140.

In an embodiment, server 120 includes optimized pollination program 101, which further includes AI module 122. In an embodiment, optimized pollination program 101 may be configured to access various data sources, such as plant pollination database 132 and pollination policies 134 that may include personal data, content, contextual data, or information that a user does not want to be processed. Personal data includes personally identifying information or sensitive personal information as well as user information, such as location tracking or geolocation information. Processing refers to any operation, automated or unautomated, or set of operations such as collecting, recording, organizing, structuring, storing, adapting, altering, retrieving, consulting, using, disclosing by transmission, dissemination, or otherwise making available, combining, restricting, erasing, or destroying personal data. In an embodiment, optimized pollination program 101 enables the authorized and secure processing of personal data. In an embodiment, optimized pollination program 101 provides informed consent, with notice of the collection of personal data, allowing the user to opt in or opt out of processing personal data. Consent can take several forms. Opt-in consent can impose on the user to take an affirmative action before personal data is processed. Alternatively, opt-out consent can impose on the user to take an affirmative action to prevent the processing of personal data before personal data is processed. In an embodiment, optimized pollination program 101 provides information regarding personal data and the nature (e.g., type, scope, purpose, duration, etc.) of the processing. In an embodiment, optimized pollination program 101 provides a user with copies of stored personal data. In an embodiment, optimized pollination program 101 allows for the correction or completion of incorrect or incomplete personal data. In an embodiment, optimized pollination program 101 allows for the immediate deletion of personal data.

In an embodiment, AI module 122 is a computer algorithm used to perform image analysis of an image of a plant. In an embodiment, optimized pollination program 101 receives an image of a plant and AI module 122 performs image analysis on the received image. In an embodiment, optimized pollination program 101 determines if a plant requires pollination. For example, optimized pollination program 101 determines if a plant is exhibiting qualities of a plant requiring pollination, such as a fully bloomed flower. In an embodiment, optimized pollination program 101 classifies a plant in an image by the type of plant or stage of blooming. For example, optimized pollination program 101 utilizes AI module 122 to perform image analysis and identifies the type of plant in an image and the classification of a blooming stage of the plant.

Figure 4:
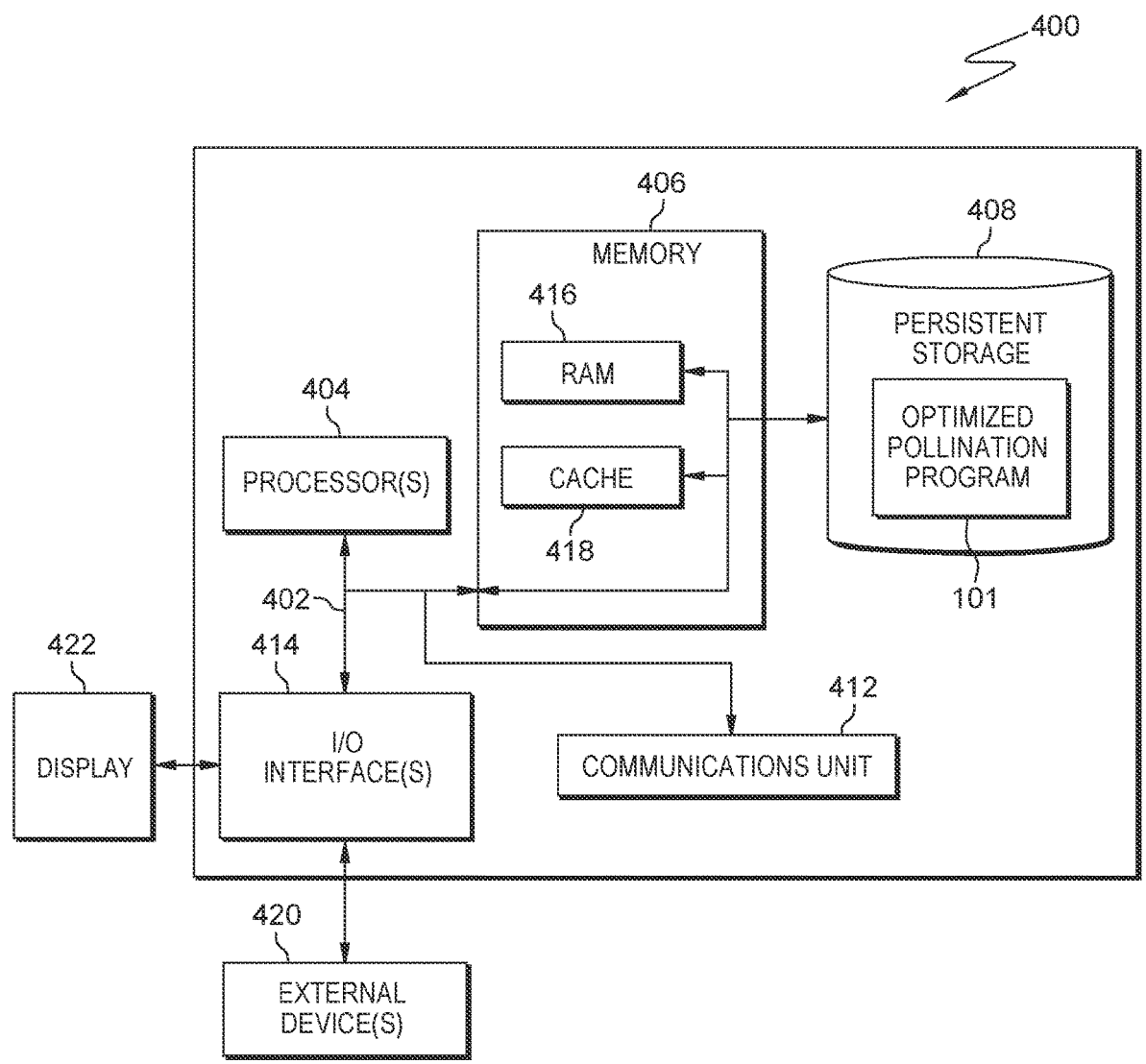
FIG. 4 is a block diagram depicting components of a computer, generally designated 400, suitable for executing an optimized pollination program 101 in accordance with at least one embodiment of the present invention.
Figure 5:
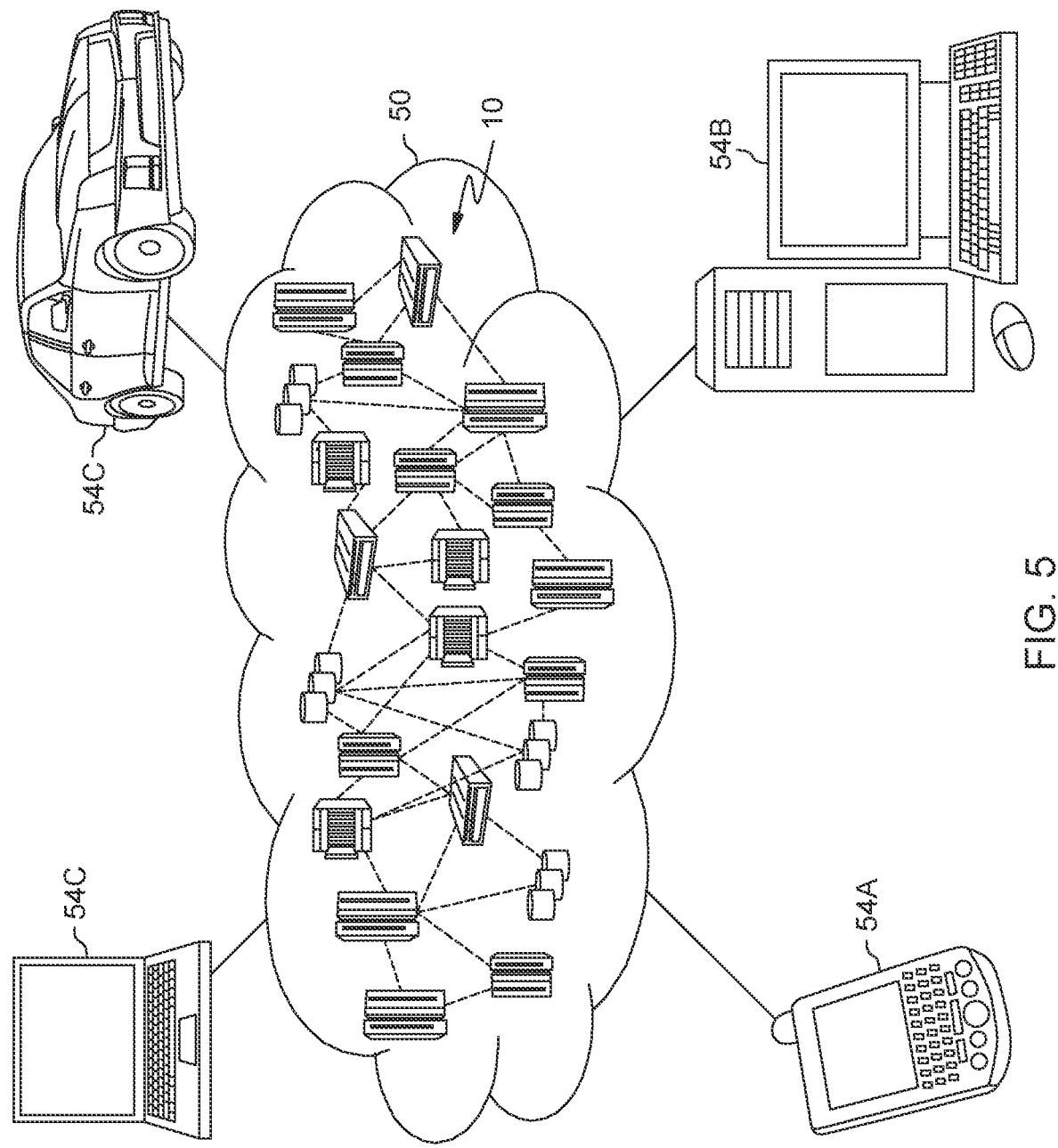
FIG. 5 is a block diagram depicting a cloud computing environment 50 in accordance with at least one embodiment of the present invention.

Server 120 may include components as depicted and described in detail with respect to cloud computing node 10, as described in reference to FIG. 5, in accordance with at least one embodiment of the present invention. Server 120 may include components, as depicted and described in detail with respect to computing device 400 of FIG. 4, in accordance with at least one embodiment of the present invention.

In various embodiments, storage device 130 is a secure data repository for persistently storing plant pollination database 132 and pollination policies 134 utilized by various applications and user devices of a user, such as user device 110. Storage device 130 may be implemented using any volatile or non-volatile storage media known in the art for storing data. For example, storage device 130 may be implemented with a tape library, optical library, one or more independent hard disk drives, multiple hard disk drives in a redundant array of independent disks (RAID), solid-state drives (SSD), random-access memory (RAM), and any possible combination thereof. Similarly, storage device 130 may be implemented with any suitable storage architecture known in the art, such as a relational database, an object-oriented database, or one or more tables.

In an embodiment, plant pollination database 132 includes various information on plant pollination. Information on plant pollination can include, for example, data, user input, photos, images, videos, pollination timelines, plant information, plant types, and optimal plant conditions. For example, user input includes information of the type of plants in the environment, their pollination timeline, and images of what the plant should look like when it is ready to be pollinated. In an embodiment, plant pollination database 132 includes information on the one or more classifications of plant pollination based, at least in part, on the blooming stage or closeness of time to require pollination of the plant. For example, the blooming stage, or flowering stage refers to the phase when a plant produces their flowers. For example, the classifications include no flowering plants present, early-stage blooming flowers, mid stage blooming flowers, and fully blossomed flowers. In an embodiment, the classifications are based on a percentage to how fully bloomed or pollinated the plant is. For example, flowering plants have different stages such as bud, bloom opening, full bloom, and dying bloom. For example, a plant with a bloom signifies the plant is pollinated and may not require further pollination and optimized pollination program 101 stores this information in plant pollination database 132. In another example, an early-stage blooming flower is a classification for plants and flowers exhibiting qualities of being 20% fully bloomed or pollinated. In an embodiment, a plant or flower exhibiting qualities being 20% fully bloomed or pollinated is a plant with a flower beginning to bud. For example, optimized pollination program 101 receives an image of the plant, performs image analysis to determine there is a flower beginning to bud, determines the plant is exhibiting qualities of being 20% fully bloomed, classifies the plant as an early-stage blooming flower, and stores the classification in plant pollination database 132.

In an embodiment, optimized pollination program 101 stores one or more images for one or more plant types in one or more plant pollination classifications in plant pollination database 132. For example, optimized pollination program 101 stores an image of a type A plant in mid stage blooming flower classification in plant pollination database 132. In an embodiment, optimized pollination program 101 accesses data in plant pollination database 132 to compare to data of current plants in the environment. For example, optimized pollination program 101 accesses an image of plant type B in fully blossomed flower stage in plant pollination database 132 to compare to an image of a current plant type B in the environment. In an embodiment, the database is updated as the machine learning model is updated.

In an embodiment, optimized pollination program 101 accesses plant pollination database 132 to determine pollination requirements for a type of plant. For example, if optimized pollination program 101 determines there is a peach tree in the environment, optimized pollination program 101 accesses plant pollination database 132 to determine pollination requirements for a peach tree. In an embodiment, pollination requirements include ideal classification for pollination, ideal weather, or ideal temperature for pollination for a particular type of plant.

In an embodiment, pollination policies 134 includes a dynamic set of rules for determining plant pollination parameters, information included in plant pollination database 132, and external environmental factors. External environmental factors may include the temperature, airflow direction, airflow speed, weather, sunlight, humidity, pressure, presence of an animal, such as a bee, or any other external environmental factor which can affect plant pollination. In an embodiment, pollination policies 134 includes information describing different decision-making actions that optimized pollination program 101 should perform depending on, for example, the particular type of plant, presence of bees, presence of airflow, velocity or speed of airflow, direction of airflow, sunlight, and other environmental factors, information included in plant pollination database 132, and the surrounding environment in which the plants are located.

In an embodiment, sensor 150 can be any type or types of sensor, such as a wind speed sensor, camera, video recorder, IoT device, microphone, drone or thermometer capable of determining or capturing environmental data, including the wind speed, wind direction, pictures, video, sound, or the temperature of the environment and plants within the environment. In various embodiments, various sensors are placed throughout the environment. For example, a video camera sensor records the video of the plants growing in the environment, while a wind sensor determines the speed and direction of the wind.

In an embodiment, sensor 150 is located on or near the plants to measure pollination process variables such as shaking and pollen. For example, if a bee lands on a flower to pollinate the flower, the plant may shake. In an embodiment, sensor 150 measures vibration of the plant signifying wind/airflow impact to simulate pollination, manual human or robotic pollination of plant, wind or air flow speed and frequency, sound and presence of bees, butterflies or other insects, and measure pollen on plants or nectar availability.

In an embodiment, optimized pollination program 101 is used in a closed environment such as a greenhouse or indoor facility. In an embodiment, optimized pollination program 101 utilizes cameras, either stationary or a drone, to capture one or more images or videos of the environment and the plants located therein. In an embodiment, optimized pollination program 101 utilizes an IoT device with a microphone to capture the sound and measure the airflow. In an embodiment, optimized pollination program 101 utilizes a fan which is programmatically controlled to turn on or off a fan, as well as change the direction, velocity, and the duration of the fan usage. In an embodiment, the fan is stationary, robotic, or drone based. For example, optimized pollination program 101 utilizes a stationary fan in the environment to point the fan east and run the fan for one hour to create a wind speed of two miles an hour. In an embodiment, optimized pollination program 101 uses video stream analysis to determine which areas of the environment need an increase in pollination. Accordingly, optimized pollination program 101 then controls the airflow in a programmatic manner to optimize pollination in the areas identified. For example, if optimized pollination program 101 determines the southeast corner of the environment needs an increase in pollination, optimized pollination program 101 controls the airflow in a programmatic manner to optimize pollination in the southeast corner of the environment.

In an embodiment, optimized pollination program 101 monitors the plants in the environment. In an embodiment, optimized pollination program 101 trains a machine learning model to determine when a plant is ready for or requires pollination. For example, optimized pollination program 101 trains a machine learning model to determine what a plant should look like when the plant is ready for pollination. In an embodiment, optimized pollination program 101 utilizes machine learning to determine pollination timelines. In another embodiment, optimized pollination program 101 trains a machine learning model to determine and predict the pollination timeline of a particular type of plant. In another example, optimized pollination program 101 trains a machine learning model to predict how long from planting a seed until the plant will be ready for pollination. In an embodiment, optimized pollination program 101 trains a machine learning model to determine the effectiveness of external factors such as weather and temperatures. For example, trains a machine learning model to determine optimal weather for bees to pollinate.

In an embodiment, optimized pollination program 101 receives user input. In an embodiment, user input indicates data for the type of plants, pollination timeline, images of plants, images of pollinated plants, and other plant and pollination information. For example, a user uploads user input to optimized pollination program 101 of one or more images of what plant A should look like when it is ready to be pollinated.

In an embodiment, optimized pollination program 101 utilizes AI module 122 to perform image analysis of flowering plants to determine the need for pollination and evaluate crop yield.

In an embodiment, optimized pollination program 101 utilizes a convolutional neural network (CNN) to analyze an image. In an embodiment, CNN is utilized to provide the capability to learn multi-level features from an image. As an example, hidden layers in a CNN can identify high level features such as edges, corners, etc. Image analysis is performed from different types of camera perspectives including: wide-angle, overhead drone mounted camera, and ground level camera. The proposed system can be deployed with any available imagery source for performing AI image recognition. In an embodiment, optimized pollination program 101 utilizes CNN pattern classification to classify the type of plants captured. This classification is used to determine the pollination requirements of each type of plant. For example, optimized pollination program 101 utilizes CNN pattern classification to classify a plant as a sunflower and determines the pollination requirements for a sunflower.

In an embodiment, optimized pollination program 101 utilizes an algorithm, such as support-vector machine (SVM), to analyze the output from the CNN. In an embodiment, support-vector machines are supervised learning models with associated learning algorithms that analyze data for classification and regression analysis. In an embodiment, optimized pollination program 101 utilizes a SVM to determine one or more types of plants in an image. For example, optimized pollination program 101 receives an image and utilizes SVM to determine an apple tree is in the image. In an embodiment, optimized pollination program 101 utilizes a SVM to classify a plant as belonging to one or more pollination stages or the need to be pollinated. In an embodiment, the classifications are based on a percentage to fully bloomed or pollinated the plant is. For example, an early-stage blooming flowers is a classification for plants and flowers exhibiting qualities of being 20% fully bloomed or pollinated. In an embodiment, a plant or flower exhibiting qualities being 20% fully bloomed or pollinated is a plant with a flower beginning to bud. For example, optimized pollination program 101 receives an image of the plant and utilizes a SVM to determine the plant in the image is 60% fully bloomed and optimized pollination program 101 classifies the plant as a mid-stage blooming flower.

In an embodiment, optimized pollination program 101, CNN processing determines the density of bees present within the captured image frames. In an embodiment, SVM classification derives the density of bees in a given area. These density measurements are used to determine how much airflow is needed for adequate pollination of the crop. In an embodiment, the number of bees present in a given area is also used to determine which type of sensor or camera perspectives/angles need to be captured depending on the location and size of the bee population relative to the flower covered area. For example, an overhead drone mounted camera would be the preferred perspective when the bee population is in close proximity to the ceiling, whereas a ground level camera provides better resolution when bees are present near the floor.

In an embodiment, optimized pollination program 101 performs image analysis to track the blooming of plant flowers in the enclosed farming environment. In an embodiment, based on historical learning or with pre-configuration information, optimized pollination program 101 identifies the correct start time and duration for optimized pollination. For example, optimized pollination program 101 determines a carrot plant is at early stage blooming flower and further determines the carrot plant will be at fully blossomed flower in 10 days. In an embodiment, optimized pollination program 101 identifies when a flower is blooming and the maturity level of the flowers. For example, optimized pollination program 101 determines a tomato plant has multiple flowers and further determines the flowers are fully matured. In an embodiment, optimized pollination program 101 identifies which flowers are in a pollination state and which flowers can start pollination. For example, optimized pollination program 101 determines the tomato plants in the environment are classified as mid stage blooming flowers and requires pollination while the corn plants in the environment are classified as no flowering plants present and do not require pollination yet. In an embodiment, optimized pollination program 101 identifies the concentration of the flowers in the enclosed greenhouse environment within specific areas. For example, optimized pollination program 101 determines with image analysis 30 watermelon plant flowers in the north end of the environment and 20 pumpkin plant flowers in the south end of the environment.

In an embodiment, optimized pollination program 101 determines the current airflow parameters in the environment based on one or more sensors 150. For example, a wind sensor determines the speed and direction of the wind in the environment. In an embodiment, current airflow parameters include wind speed, wind direction, or wind velocity.

In an embodiment, optimized pollination program 101 determines the required airflow parameters for optimal pollination based, at least in part, on the current airflow parameters, the type of plant, the classification stage of the plant, and current occupancy of bees within a predetermined area of the plant. In an embodiment, optimized pollination program 101 selects a policy to determine the required airflow parameters for optimal pollination based, at least in part, on the current airflow parameters, the type of plant, the classification stage of the plant, and current occupancy of bees within a predetermined area of the plant. In an embodiment, the required airflow parameters include, but are not limited to, airflow speed, airflow direction, airflow velocity, or time of airflow.

In an embodiment, optimized pollination program 101 programmatically controls the airflow to optimize plant pollination. In an embodiment, optimized pollination program 101 enables air flow from stationary fans or devices for the time, duration, and velocity determined for optimal pollination. For example, optimized pollination program 101 determines that the squash plants are at fully bloomed stage, with bees present, and the current airflow is 1 mph. Here, optimized pollination program 101 selects a policy for squash plants at bloomed stage, with bees present, and with current airflow of 1 mph. In this example, the policy indicates the current airflow should be 5 mph and optimized pollination program 101 adjusts the air flow from stationary fans to generate airflow to a controlled airflow of 5 mph.

In an embodiment, optimized pollination program 101 selectively routes one or more fans to generate controlled air flow as needed to areas in need of optimized plant pollination that are not accessible from stationary air flow control. In an embodiment, optimized pollination program 101 continuously validates the level of the pollination is above a predetermined threshold in the surrounding areas. In an embodiment, the threshold level of pollination is based, at least in part, on the classification of the plant. In an embodiment, optimized pollination program 101 continuously applies the controlled airflow in the surrounding areas to maximize the pollination.

In an embodiment, optimized pollination program 101 validates the level of pollination is above a predetermined threshold within specific areas identified in the environment and determines how long the airflow is to be artificially produced. In an embodiment, optimized pollination program 101 validates the completeness of pollination by determining a dead plant or a growing vegetable, fruit, or plant via image analysis. For example, if a purple eggplant is in the image of a previous eggplant plant, optimized pollination program 101 determines a vegetable is growing and pollination is no longer required for that plant. In an embodiment, optimized pollination program 101 performs image analysis of the flowers to predict the level of completeness of pollination of the flowers in the greenhouse farming coverage area, and accordingly controls the airflow parameters for complete pollination.

In an embodiment, optimized pollination program 101 validates the level of pollination by comparing plant pollination information with the current plant pollination state. In an embodiment, plant pollination database 132 includes information on different plant states including preceding pollination, various states of pollination, and post pollination growth. In an embodiment, optimized pollination program 101 compares the current plant pollination state with known states in plant pollination database 132. For example, depending on the plant type it may initially only show 1 flower for the plant on day X, and on day Y show 5 flowering buds, etc.

In an embodiment, optimized pollination program 101 validates the level of pollination using sensor data based measurements of pollination. In an embodiment, the level of pollination is based, at least in part on the percentage of pollination or classification. In an embodiment, optimized pollination program 101 captures and analyzes data used to measure plant pollination status using AI module 122. In an embodiment, the sensor data collected can be directly or indirectly correlated to the pollination status of a plant. In an embodiment, optimized pollination program 101 validates the level of pollination by the k nearest neighbor by correlating the sensor readings to a known pollination statuses. For example, if the majority of plants with a given vibration sensor reading are observed to be pollinated, then AI module 122 can assume that the current plant with the similar vibration sensor is also pollinated.

In an embodiment, optimized pollination program 101 validates the level of pollination by a statistical method to find the best fit line for a dataset. This line can be used to make predictions about new data points. For example, if a linear regression model shows that there is a positive relationship between airflow speed and pollination, then optimized pollination program 101 predicts that increasing the airflow speed will increase pollination.

In an embodiment, optimized pollination program 101 validates the level of pollination by a machine learning algorithm, such as a SVM, that can be used to find the decision boundary for a dataset. This boundary can be used to make predictions about new data points. For example, if a SVM model shows that there is a positive relationship between temperature and pollination, then optimized pollination program 101 can predict that increasing the temperature will increase pollination.

In an embodiment, optimized pollination program 101 validates the level of pollination by a random forest machine learning algorithm that can be used to find the most important features for a dataset. These features can be used to make predictions about new data points. For example, if the random forest model shows that airflow is the most important feature for pollination, then optimized pollination program 101 can predict that a change in airflow will result in a change in pollination.

In an embodiment, optimized pollination program 101 validates the level of pollination by a Naive Bayes machine learning algorithm that can be used to find the probability of a datapoint belonging to a certain class. For example, if the Naive Bayes model shows that there is a 70% chance of a plant being pollinated given that the airflow speed is 5 m/s, then optimized pollination program 101 can predict that the plant is likely to be pollinated.

In an embodiment, optimized pollination program 101 determines AI learned airflow parameters and stores them in plant pollination database 132. In an embodiment, while airflow-based pollination is in progress, optimized pollination program 101 measures the effectiveness of the pollination and identifies whether airflow parameters need to be changed. In an embodiment, optimized pollination program 101 performs image analysis to identify when the pollination of a plant is complete. In an embodiment, once the pollination is completed, then optimized pollination program 101 stops the airflow which is used for optimized pollination. In an embodiment, optimized pollination program 101 performs image analysis to evaluate the crop yield based on the air flow parameters used for pollination as a measure of effectiveness. In an embodiment, optimized pollination program 101 stores the learned air flow for optimized pollination and crop yield in plant pollination database 132.

In an embodiment, optimized pollination program 101 determines the air pressure or barometric pressure within a predetermined area of a plant. In an embodiment, the optimal pollination parameters are based, at least in part, on the determined air pressure or barometric pressure within the predetermined area of the plant. In an embodiment, optimized pollination program 101 is able to accommodate fluctuations within the barometric pressure (air pressure), thus utilizing said changes in the best possible way. Changes outside of the environment may affect the environment in various means. Utilization of the air pressure changes can be known, calculated, forecasted, and utilized to the benefit of the modeling derived.

In an embodiment, optimized pollination program 101 determines the ground elevation level of a plant. In an embodiment, the optimal pollination parameters are based, at least in part, on the determined ground elevation level of the pant. For example, high altitude gardening has various types of key elements that must be considered to maintain the proper environment for plants being grown at high altitudes. In an embodiment, forced air ventilation of the greenhouse and cooling are vital parts of maintaining the correct temperature within the greenhouse and must be considered when manipulating the airflow patterns within the greenhouse.

In an embodiment, optimized pollination program 101 monitors an enclosed farming environment. In an embodiment, optimized pollination program 101 monitors an area of the environment containing plants. For example, optimized pollination program 101 monitors an area by receiving video or images from a camera. In an embodiment, optimized pollination program 101 extracts from the video or image, physical features of the plants. In an embodiment, optimized pollination program 101 extracts physical features of the plant from the video or image by performing image analysis on an agricultural image to determine a type of one or more plants in the agricultural image and a classification of one or more plants in the agricultural image. In an embodiment, optimized pollination program 101 determines pollination requirements of the one or more plants in the agricultural image based on the physical features. In an embodiment, optimized pollination program 101 selects a pollination policy based on the physical features of the plant. In an embodiment, optimized pollination program 101 performs image analysis on an agricultural image to determine a density of bees in the area around the plants. In an embodiment, optimized pollination program 101 selects a pollination policy based on the density of bees in the area around the plant.

In an embodiment, optimized pollination program 101 collects data from an airflow sensor in the area. In an embodiment, optimized pollination program 101 selects a pollination policy based on the data from an airflow sensor in the area. In an embodiment, optimized pollination program 101 determines optimal airflow parameters within a predetermined area of the environment for the one or more plants in the agricultural image based on the monitoring. In an embodiment, determining one or more optimal airflow parameters based, at least in part, on the type of one or more plants in the agricultural image, the classification of one or more plants in the agricultural image, the one or more pollination requirements for the one or more determined plants in the agricultural image, and the one or more current airflow parameters.

In an embodiment, optimized pollination program 101 collects growth data from the plants while continuing the monitoring and adjusting the airflow to the optimal airflow. In an embodiment, optimized pollination program 101 adjust the optimal airflow parameters based, at least in part, on the density of bees in the agricultural image.

In an embodiment, optimized pollination program 101 generates an automatic airflow adjustment model for optimizing the airflow parameters based on the pollination requirements, the bee density, and the growth data. In an embodiment, optimized pollination program 101 generates an automatic airflow adjustment model for optimizing the airflow parameters for the one or more determine plants based, at least in part, on the one or more determined optimal airflow parameters.

In an embodiment, optimized pollination program 101 compares the type of one or more plants in the agricultural image with one or more types of plants in previous agricultural images. In an embodiment, optimized pollination program 101 determines a previous crop yield resulting from the one or more types of plants in the previous agricultural images. In an embodiment, optimized pollination program 101 performs image analysis to evaluate the crop yield for the one or more plants in the agricultural image based on the optimal air flow parameters used for pollination to determine an effectiveness of the determined optimal airflow parameters. In an embodiment, optimized pollination program 101 compares previous air flow parameters for the one or more types of plants in the previous agricultural image and the one or more current airflow parameters within the predetermined area of the one or more plants in the agricultural image. In an embodiment, optimized pollination program 101 adjusts the optimal airflow parameters based, at least in part, on the comparison of the previous crop yield and the previous air flow parameters with the current airflow parameters.

In an embodiment, optimized pollination program 101 programmatically controls one or more wind flow parameters within at least one of an area within the predetermined area of the one or more plants in the agricultural image or a predetermined area outside of the predetermined area of the one or more plants in the agricultural image based, at least in part, on the determined optimal set of airflow parameters. In an embodiment, optimized pollination program 101 programmatically controls one or more wind flow parameters by controlling a fan to generate airflow.

In an embodiment, optimized pollination program 101 performs image analysis on the agricultural image to determine an optimal start time and duration for optimal pollination. In an embodiment, the optimal start time and duration for optimal pollination comprises controlling the one or more airflow parameters dynamically modified based on a repeated analysis of the state of pollination of the one or more plants in the agricultural image. In an embodiment, when it is the optimal start time for optimal pollination, optimized pollination program 101 turns on a fan or other device to control the airflow parameters. In an embodiment, when the optimal start time for optimal pollination has expired, optimized pollination program 101 turns off the fan or other device to control the airflow parameters.

Figure 2:
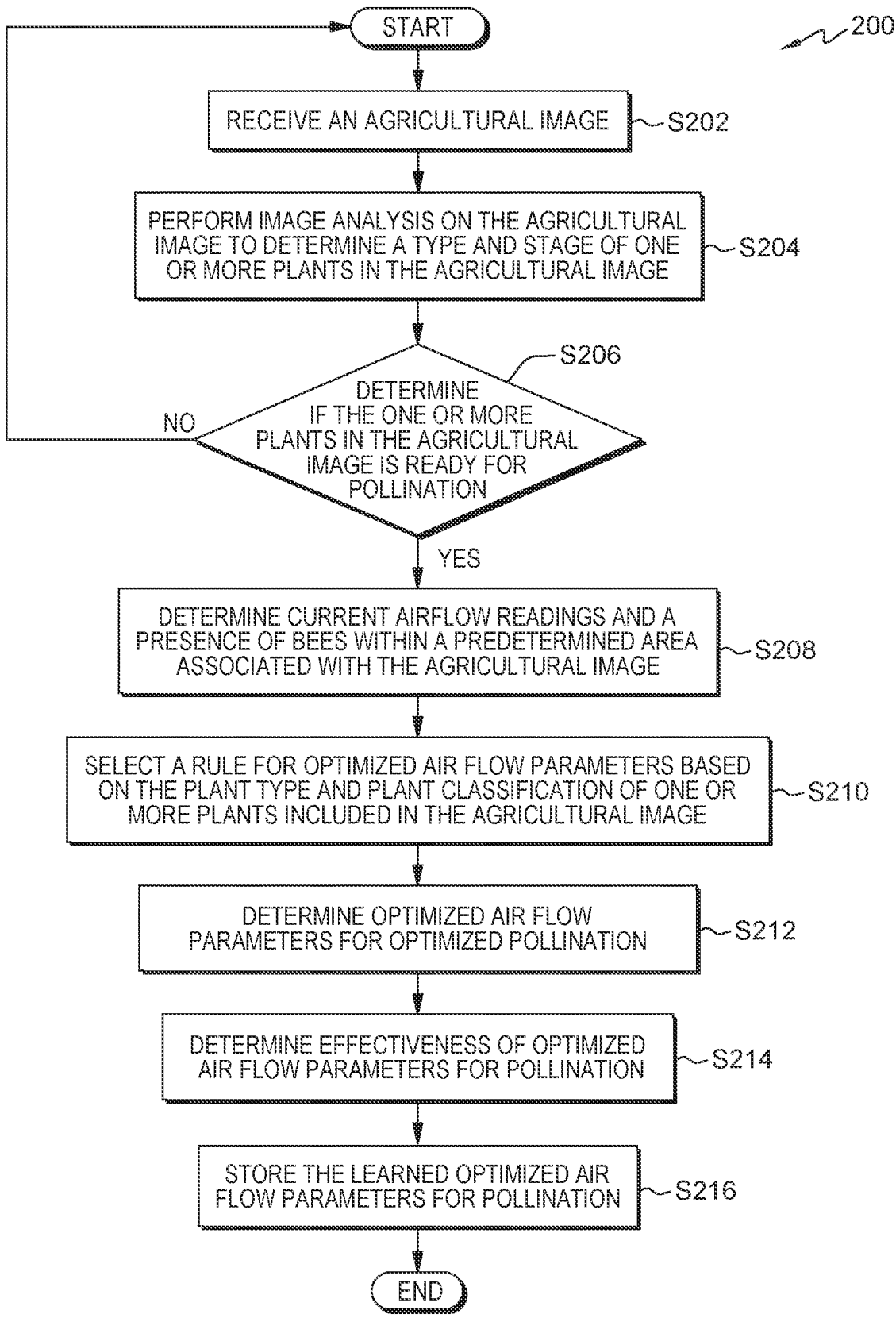
FIG. 2 is a flow chart diagram depicting operational steps for optimized pollination program 101, generally designated 200, in accordance with at least one embodiment of the present invention.

FIG. 2 is a flow chart diagram depicting operational steps for optimized pollination program 101, generally designated 200, in accordance with at least one embodiment of the present invention. FIG. 2 provides only an illustration of one implementation and does not imply any limitations with regard to the environments in which different embodiments may be implemented. Many modifications to the depicted environment may be made by those skilled in the art without departing from the scope of the invention as recited by the claims.

At step S202, optimized pollination program 101 receives an agricultural image. In an embodiment, optimized pollination program 101 receives an agricultural image from a camera or other sensor.

At step S204, optimized pollination program 101 performs image analysis on the agricultural image to determine a type and stage of one or more plants in the agricultural image.

At decision step S206, optimized pollination program 101 determines if the one or more plants in the agricultural image is ready for pollination. In an embodiment, optimized pollination program 101 determines if the one or more plants in the agricultural image is ready for pollination based, at least in part, on the level of pollination. In an embodiment, optimized pollination program 101 determines if a plant in the agricultural image is exhibiting qualities of a plant requiring or ready for pollination, such as a fully bloomed flower. In an embodiment, optimized pollination program 101 classifies a plant in the agricultural image by the type of plant or stage of blooming. For example, optimized pollination program 101 utilizes AI module 122 to perform image analysis and identifies the type of plant in the agricultural image and the classification or stage of blooming. In an embodiment, optimized pollination program 101 determines if a plant is ready for pollination based, at least in part, on the classification. If optimized pollination program 101 determines that one or more plants in the agricultural image are not ready for pollination (decision step S206 "NO" branch), optimized pollination program 101 returns to step S202. If optimized pollination program 101 determines that one or more plants in the agricultural image are ready for pollination (decision step S206 "YES" branch), optimized pollination program 101 proceeds to step S208.

At step S208, optimized pollination program 101 determines current airflow readings and a presence of bees within a predetermined area associated with the agricultural image. In an embodiment, optimized pollination program 101 determines the location and density of bees within a predetermined area associated with the agricultural image based on image analysis. In an embodiment, optimized pollination program 101 determines the airflow velocity or speed of airflow and direction of airflow associated with a predetermined area associated within the agricultural image.

At step S210, optimized pollination program 101 selects a rule for optimized air flow parameters based on the plant type and plant classification of one or more plants included in the agricultural image. In an embodiment, optimized pollination program 101 selects a rule for optimized air flow parameters based, at least in part, on the presence of bees within the predetermined area associated with the agricultural image and/or a presence of bees located outside the predetermined area associated with the agricultural image.

At step S212, optimized pollination program 101 determines optimized air flow parameters for optimized pollination. In an embodiment, optimized pollination program 101 determines optimized air flow parameters for optimized pollination based, at least in part, on the selected rule.

At step S214, optimized pollination program 101 determines an effectiveness of the optimized airflow parameters for pollination. In an embodiment, optimized pollination program 101 tracks and learns the effectiveness of pollination by evaluating the yield of crops, based on the applied air flow parameters, accordingly, to create a knowledge corpus to identify how to optimize pollination based on the applied air flow parameters for the type of plants included in the agricultural image.

At step S216, optimized pollination program 101 stores the learned optimized air flow parameters for pollination. In an embodiment, optimized pollination program 101 stores the learned air flow parameters for optimized pollination and crop yields in plant pollination database 132.

Figure 3:
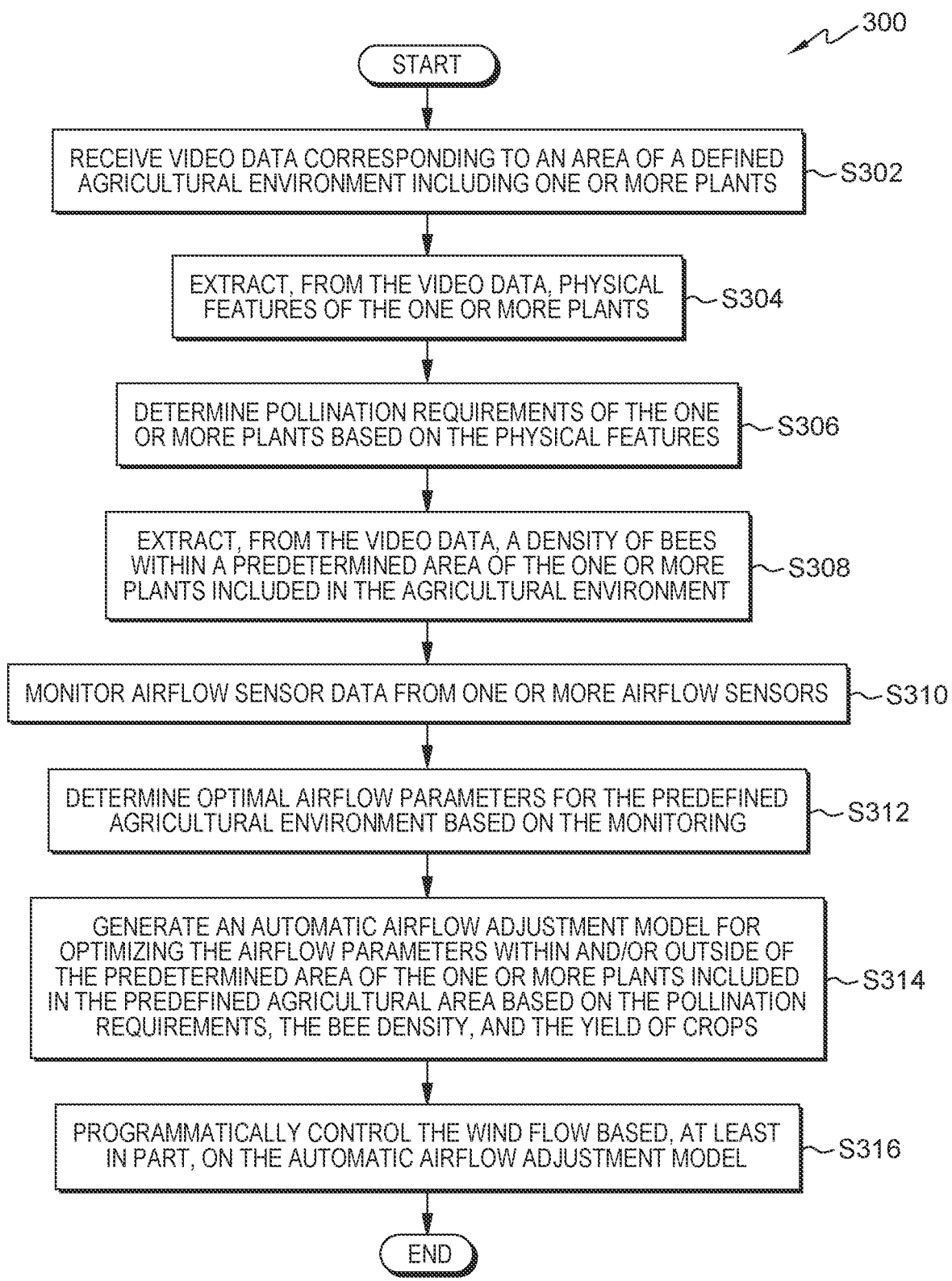
FIG. 3 is a flow chart diagram depicting operational steps for optimized pollination program 101, generally designated 300, in accordance with at least one embodiment of the present invention.

FIG. 3 is a flow chart diagram depicting operational steps for optimized pollination program 101, generally designated 300, in accordance with at least one embodiment of the present invention. FIG. 3 provides only an illustration of one implementation and does not imply any limitations with regard to the environments in which different embodiments may be implemented. Many modifications to the depicted environment may be made by those skilled in the art without departing from the scope of the invention as recited by the claims.

At step 302, optimized pollination program 101 receives video data corresponding to an area of a defined agricultural environment including one or more plants.

At step 304, optimized pollination program 101 extracts, from the video data, physical features of the one or more plants. In an embodiment, optimized pollination program 101 performs image analysis on images taken from the video data to determine physical features of the plant.

At step 306, optimized pollination program 101 determines pollination requirements of the one or more plants based on the physical features.

At step 308, optimized pollination program 101 extracts, from the video data, a density of bees within a predetermined area of the one or more plants included in the agricultural environment. In an embodiment, optimized pollination program 101 determines the location and number of the bees both within the predetermined area and outside of the predetermined area of the one or more plants included in the agricultural environment.

At step 310, optimized pollination program 101 monitors airflow sensor data from one or more airflow sensors. In an embodiment, optimized pollination program 101 monitors airflow sensor data from airflow sensors included within the predetermined area and outside of the predetermined area of the one or more plants included in the predefined agricultural environment. In an embodiment, the airflow sensor data includes one or more of airflow speed, airflow velocity, airflow direction, temperature, humidity, sunlight, or barometric pressure.

At step 312, optimized pollination program 101 determines optimal airflow parameters for the predefined agricultural environment based on the monitoring. In an embodiment, optimized pollination program 101 selects a policy based on the detected airflow parameters to determine an optimal airflow.

At step 314, optimized pollination program 101 generates an automatic airflow adjustment model for optimizing the airflow parameters within and/or outside of the predetermined area of the one or more plants included in the predefined agricultural area based on the pollination requirements, the bee density, and the yield of crops.

At step 316, optimized pollination program 101 programmatically controls the wind flow based, at least in part, on the automatic airflow adjustment model.

FIG. 4 is a block diagram depicting components of a computing device, generally designated 400, suitable for optimized pollination program 101 in accordance with at least one embodiment of the invention. Computing device 400 includes one or more processor(s) 404 (including one or more computer processors), communications fabric 402, memory 406 including, RAM 416 and cache 418, persistent storage 408, which further includes optimized pollination program 101, communications unit 412, I/O interface(s) 414, display 422, and external device(s) 420. It should be appreciated that FIG. 4 provides only an illustration of one embodiment and does not imply any limitations with regard to the environments in which different embodiments may be implemented. Many modifications to the depicted environment may be made.

As depicted, computing device 400 operates over communications fabric 402, which provides communications between computer processor(s) 404, memory 406, persistent storage 408, communications unit 412, and input/output (I/O) interface(s) 414. Communications fabric 402 can be implemented with any architecture suitable for passing data or control information between processor(s) 404 (e.g., microprocessors, communications processors, and network processors), memory 406, external device(s) 420, and any other hardware components within a system. For example, communications fabric 402 can be implemented with one or more buses.

Memory 406 and persistent storage 408 are computer readable storage media. In the depicted embodiment, memory 406 includes random-access memory (RAM) 416 and cache 418. In general, memory 406 can include any suitable volatile or non-volatile computer readable storage media.

Program instructions for optimized pollination program 101 can be stored in persistent storage 408, or more generally, any computer readable storage media, for execution by one or more of the respective computer processor(s) 404 via one or more memories of memory 406. Persistent storage 408 can be a magnetic hard disk drive, a solid-state disk drive, a semiconductor storage device, read-only memory (ROM), electronically erasable programmable read-only memory (EEPROM), flash memory, or any other computer readable storage media that is capable of storing program instructions or digital information.

Media used by persistent storage 408 may also be removable. For example, a removable hard drive may be used for persistent storage 408. Other examples include optical and magnetic disks, thumb drives, and smart cards that are inserted into a drive for transfer onto another computer readable storage medium that is also part of persistent storage 408.

Communications unit 412, in these examples, provides for communications with other data processing systems or devices. In these examples, communications unit 412 can include one or more network interface cards. Communications unit 412 may provide communications through the use of either or both physical and wireless communications links. In the context of some embodiments of the present invention, the source of the various input data may be physically remote to computing device 400 such that the input data may be received, and the output similarly transmitted via communications unit 412.

I/O interface(s) 414 allows for input and output of data with other devices that may operate in conjunction with computing device 400. For example, I/O interface(s) 414 may provide a connection to external device(s) 420, which may be as a keyboard, keypad, a touch screen, or other suitable input devices. External device(s) 420 can also include portable computer readable storage media, for example thumb drives, portable optical or magnetic disks, and memory cards. Software and data used to practice embodiments of the present invention can be stored on such portable computer readable storage media and may be loaded onto persistent storage 408 via I/O interface(s) 414. I/O interface(s) 414 also can similarly connect to display

422. Display 422 provides a mechanism to display data to a user and may be, for example, a computer monitor.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

FIG. 5 is a block diagram depicting a cloud computing environment 50 in accordance with at least one embodiment of the present invention. Cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 10 and cloud computing environment 50 can communicate with any type of computerized device over any type of network and/or network addressable connection (e.g., using a web browser).

Figure 6:
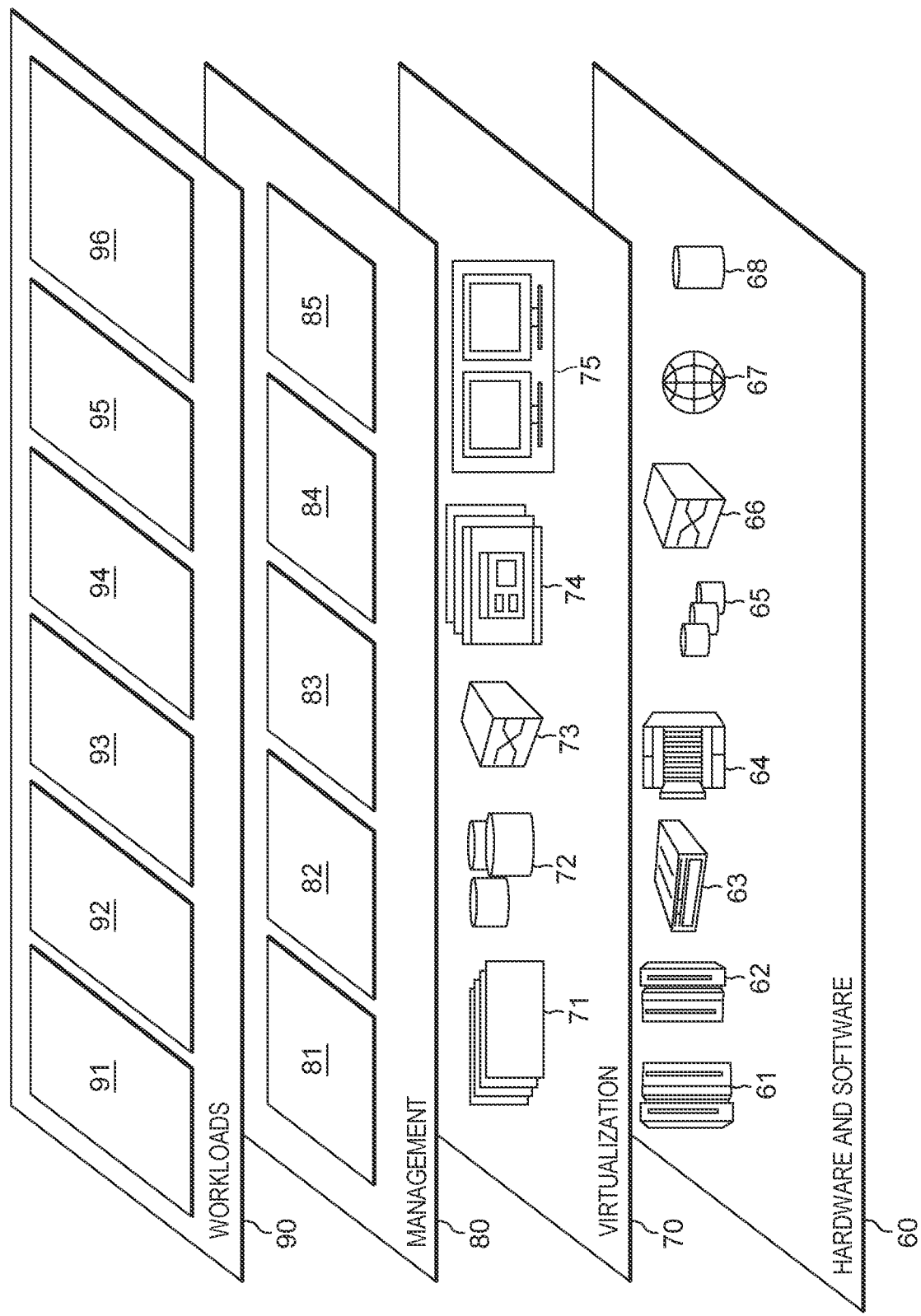
FIG. 6 is block diagram depicting a set of functional abstraction model layers provided by cloud computing environment 50 depicted in FIG. 5 in accordance with at least one embodiment of the present invention.

FIG. 6 is block diagram depicting a set of functional abstraction model layers provided by cloud computing environment 50 depicted in FIG. 5 in accordance with at least one embodiment of the present invention. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and pollination airflow parameters 96.

What is claimed is:

1. A computer-implemented method for airflow control for agricultural pollination, the computer-implemented method comprising:
    performing image analysis on an agricultural image to determine a type of one or more plants in the agricultural image and a classification of one or more plants in the agricultural image;
    determining one or more pollination requirements for the one or more determined plants in the agricultural image;
    determining one or more current airflow parameters within a predetermined area of the one or more plants in the agricultural image;
    determining one or more optimal airflow parameters based, at least in part, on the type of one or more plants in the agricultural image, the classification of one or more determined plants in the agricultural image, the one or more pollination requirements for the one or more determined plants in the agricultural image, and the one or more current airflow parameters, wherein determining the one or more optimal air flow parameters comprises comparing the type of one or more plants in the agricultural image with one or more types of plants in previous agricultural images, determining a previous crop yield resulting from the one or more types of plants in the previous agricultural images, comparing previous air flow parameters for the one or more types of plants in the previous agricultural image and the one or more current airflow parameters, and determining the optimal airflow parameters based, at least in part, on a comparison of the previous crop yield and the previous air flow parameters with the current airflow parameters; and
    generating an automatic airflow adjustment model for optimizing the airflow parameters for the one or more determined plants based, at least in part, on the one or more determined optimal airflow parameters.

2. The computer-implemented method of claim 1, wherein determining an optimal airflow parameter is further based, at least in part, on:
    performing image analysis on the agricultural image to determine a density of bees in the agricultural image; and
    adjusting the optimal airflow parameters based, at least in part, on the density of bees in the agricultural image.

3. The computer-implemented method of claim 2, wherein adjusting the optimal airflow parameters is further based on a location of the density of bees within the predetermined area of the one or more plants in the agricultural image.

4. The computer-implemented method of claim 1, wherein determining the one or more optimal air flow parameters further comprises:
    performing image analysis to evaluate the crop yield for the one or more plants in the agricultural image based on the optimal air flow parameters used for pollination to determine an effectiveness of the determined optimal airflow parameters.

5. The computer-implemented method of claim 1, further comprising: programmatically controlling one or more wind flow parameters within at least one of an area within the predetermined area of the one or more plants in the agricultural image or a predetermined area outside of the predetermined area of the one or more plants in the agricultural image based, at least in part, on the determined optimal set of airflow parameters.

6. The computer-implemented method of claim 1, further comprising:
    performing image analysis on the agricultural image to determine an optimal start time and duration for optimal pollination, wherein the optimal start time and duration for optimal pollination comprises controlling the one or more airflow parameters dynamically modified based on a repeated analysis of a state of pollination of the one or more plants in the agricultural image.

7. A computer program product for airflow control for agricultural pollination, the computer program product comprising one or more computer readable storage media and program instructions stored on the one or more computer readable storage media, the program instructions including instructions to:
    perform image analysis on an agricultural image to determine a type of one or more plants in the agricultural image and a classification of one or more plants in the agricultural image;
    determine one or more pollination requirements for the one or more determined plants in the agricultural image;
    determine one or more current airflow parameters within a predetermined area of the one or more plants in the agricultural image;

determine one or more optimal airflow parameters based, at least in part, on the type of one or more plants in the agricultural image, the classification of one or more determined plants in the agricultural image, the one or more pollination requirements for the one or more determined plants in the agricultural image, and the one or more current airflow parameters, wherein the program instructions that determine the one or more optimal air flow parameters include instructions to compare the type of one or more plants in the agricultural image with one or more types of plants in previous agricultural images, determine a previous crop yield resulting from the one or more types of plants in the previous agricultural images, compare previous air flow parameters and the one or more current airflow parameters within the predetermined area of the one or more plants in the agricultural image, and determine the optimal airflow parameters based, at least in part, on a comparison of the previous crop yield and the previous air flow parameters with the current airflow parameters; and generate an automatic airflow adjustment model for optimizing the airflow parameters for the one or more determined plants based, at least in part, on the one or more determined optimal airflow parameters.

8. The computer program product of claim 7, wherein instructions to determine an optimal airflow parameter is further based, at least in part, on instructions to:
perform image analysis on the agricultural image to determine a density of bees in the agricultural image; and
adjust the optimal airflow parameters based, at least in part, on the density of bees in the agricultural image.

9. The computer program product of claim 8, wherein adjusting the optimal airflow parameters is further based on a location of the density of bees within the predetermined area of the one or more plants in the agricultural image.

10. The computer program product of claim 7, wherein the program instructions that determine the one or more optimal air flow parameters further include instructions to:
perform image analysis to evaluate the crop yield for the one or more plants in the agricultural image based on the optimal air flow parameters used for pollination to determine an effectiveness of the determined optimal airflow parameters.

11. The computer program product of claim 7, further comprising instructions to:
programmatically control one or more wind flow parameters within at least one of an area within the predetermined area of the one or more plants in the agricultural image or a predetermined area outside of the predetermined area of the one or more plants in the agricultural image based, at least in part, on the determined optimal set of airflow parameters.

12. The computer program product of claim 7, further comprising instructions to:
perform image analysis on the agricultural image to determine an optimal start time and duration for optimal pollination, wherein the optimal start time and duration for optimal pollination comprises controlling the one or more airflow parameters dynamically modified based on a repeated analysis of a state of pollination of the one or more plants in the agricultural image.

13. A computer system for airflow control for agricultural pollination, comprising:
one or more computer processors;
one or more computer readable storage media; and
computer program instructions,
the computer program instructions being stored on the one or more computer readable storage media for execution by the one or more computer processors,
the computer program instructions including instructions to:
perform image analysis on an agricultural image to determine a type of one or more plants in the agricultural image and a classification of one or more plants in the agricultural image;
determine one or more pollination requirements for the one or more determined plants in the agricultural image;
determine one or more current airflow parameters within a predetermined area of the one or more plants in the agricultural image;
determine one or more optimal airflow parameters based, at least in part, on the type of one or more plants in the agricultural image, the classification of one or more determined plants in the agricultural image, the one or more pollination requirements for the one or more determined plants in the agricultural image, and the one or more current airflow parameters, wherein the computer program instructions that determine the one or more optimal air flow parameters include instructions to compare the type of one or more plants in the agricultural image with one or more types of plants in previous agricultural images, determine a previous crop yield resulting from the one or more types of plants in the previous agricultural images, compare previous air flow parameters and the one or more current airflow parameters within the predetermined area of the one or more plants in the agricultural image, and determine the optimal airflow parameters based, at least in part, on a comparison of the previous crop yield and the previous air flow parameters with the current airflow parameters; and
generate an automatic airflow adjustment model for optimizing the airflow parameters for the one or more determined plants based, at least in part, on the one or more determined optimal airflow parameters.

14. The computer system of claim 13, wherein instructions to determine an optimal airflow parameter is further based, at least in part, on instructions to:
perform image analysis on the agricultural image to determine a density of bees in the agricultural image; and
adjust the optimal airflow parameters based, at least in part, on the density of bees in the agricultural image.

15. The computer system of claim 14, wherein adjusting the optimal airflow parameters is further based on a location of the density of bees within the predetermined area of the one or more plants in the agricultural image.

16. The computer system of claim 15, wherein the program instructions that determine the one or more optimal air flow parameters further include instructions to:
perform image analysis to evaluate the crop yield for the one or more plants in the agricultural image based on the optimal air flow parameters used for pollination to determine an effectiveness of the determined optimal airflow parameters.

17. The computer system of claim 13, further comprising instructions to:
perform image analysis on the agricultural image to determine an optimal start time and duration for optimal pollination, wherein the optimal start time and duration for optimal pollination comprises controlling the one or more airflow parameters dynamically modified based on a repeated analysis of a state of pollination of the one or more plants in the agricultural image.

18. The computer-implemented method of claim 1, further comprising:
   determining an effectiveness of the one or more optimal air flow parameters.

19. The computer program product of claim 7, further comprising instructions to:
   determine an effectiveness of the one or more optimal air flow parameters.

20. The computer system of claim 13, further comprising instructions to:
   determine an effectiveness of the one or more optimal air flow parameters.

* * * * *